United States Patent
Slemker et al.

(10) Patent No.: US 8,308,816 B2
(45) Date of Patent: Nov. 13, 2012

(54) SEALING LINER AND LOCK FOR PROSTHETIC LIMB

(75) Inventors: Tracy C. Slemker, Clayton, OH (US); Robert Hoskins, Springboro, OH (US); Paul L. Galloway, Clayton, OH (US)

(73) Assignee: Prosthetic Design, Inc., Clayton, OH (US)

( * ) Notice: Subject to any disclaimer, the term of this patent is extended or adjusted under 35 U.S.C. 154(b) by 122 days.

(21) Appl. No.: 12/841,639

(22) Filed: Jul. 22, 2010

(65) Prior Publication Data

US 2011/0022184 A1 Jan. 27, 2011

Related U.S. Application Data

(60) Provisional application No. 61/227,889, filed on Jul. 23, 2009.

(51) Int. Cl.
*A61F 2/80* (2006.01)
(52) U.S. Cl. .......................................... 623/34
(58) Field of Classification Search ............... 623/32–37
See application file for complete search history.

(56) References Cited

U.S. PATENT DOCUMENTS

| | | | |
|---|---|---|---|
| 5,007,937 A | 4/1991 | Fishman et al. | |
| 5,728,170 A | 3/1998 | Becker et al. | |
| 5,888,216 A | 3/1999 | Haberman | |
| 6,334,876 B1 | 1/2002 | Perkins | |
| 6,508,842 B1 | 1/2003 | Caspers | |
| 6,689,171 B2 | 2/2004 | Slemker et al. | |
| 6,726,726 B2 | 4/2004 | Caspers | |
| 6,964,688 B1 | 11/2005 | Kania | |
| 7,025,793 B2 | 4/2006 | Egilsson | |
| 7,118,602 B2 | 10/2006 | Bjarnason | |
| 7,169,188 B2 | 1/2007 | Carstens | |
| 7,169,189 B2 | 1/2007 | Bjarnason et al. | |
| 7,235,108 B2 | 6/2007 | Carstens | |
| 2006/0010690 A1 | 1/2006 | Bogue | |
| 2006/0212128 A1* | 9/2006 | Nachbar | 623/24 |
| 2007/0005149 A1 | 1/2007 | Egilsson et al. | |
| 2007/0112439 A1* | 5/2007 | Panucialman | 623/26 |
| 2007/0123998 A1 | 5/2007 | Egilsson et al. | |
| 2008/0086218 A1 | 4/2008 | Egilsson | |

* cited by examiner

*Primary Examiner* — Bruce E Snow
(74) *Attorney, Agent, or Firm* — Baker & Hostetler LLP (57) ABSTRACT

Locking systems for prosthetic sockets utilizing integrated vacuum and mechanical coupling are disclosed. Some example embodiments may include a flexible liner shaped to accept a portion of a patient's residual limb, the flexible liner including a liner distal end including at least one surface feature; a plunger pin extending distally from the liner distal end; and a locking mechanism for mounting within a prosthetic limb socket approximate a socket distal end, the locking mechanism including a central opening sized to receive the plunger pin, the locking mechanism releasably engaging the plunger pin when the residual limb and the liner are inserted into the socket, wherein a proximal end of the locking mechanism includes at least one surface feature for releasably and sealingly engaging the at least one surface feature of the distal end of the flexible liner.

14 Claims, 10 Drawing Sheets

SEALING LINER AND LOCK FOR PROSTHETIC LIMB

CROSS REFERENCE TO RELATED APPLICATIONS

This application claims the benefit of U.S. Provisional Application No. 61/227,889, filed Jul. 23, 2009, which is incorporated by reference.

BACKGROUND

The present disclosure is directed to systems for releasably coupling a prosthetic device to the residual limb of an amputee. More specifically, the present disclosure includes devices utilizing integrated vacuum and mechanical coupling to provide improved retention and comfort for a prosthetic device including a socket.

SUMMARY

Exemplary embodiments may include locking systems for prosthetic sockets utilizing integrated vacuum and mechanical coupling. Some example embodiments may include a flexible liner shaped to accept a portion of a patient's residual limb, the flexible liner including a liner distal end including at least one surface feature; a plunger pin extending distally from the liner distal end; and a locking mechanism for mounting within a prosthetic limb socket approximate a socket distal end, the locking mechanism including a central opening sized to receive the plunger pin, the locking mechanism releasably engaging the plunger pin when the residual limb and the liner are inserted into the socket, wherein a proximal end of the locking mechanism includes at least one surface feature for releasably and sealingly engaging the at least one surface feature of the distal end of the flexible liner.

In an aspect, a prosthetic limb assembly may include a flexible liner shaped to accept at least a portion of a patient's residual limb, the flexible liner including an interior, an exterior, and a liner distal end including at least one surface feature; a plunger pin mounted to the liner distal end; a socket shaped to receive the liner and the patient's residual limb, the socket including a socket interior, a proximal opening for receiving the residual limb, and a socket distal end; a locking mechanism mounted within the socket distal end and including a central opening sized to receive the plunger pin, the locking mechanism releasably engaging the plunger pin when the residual limb and the liner are inserted into the socket, where a proximal end of the locking mechanism includes at least one surface feature for releasably and sealingly engaging the at least one surface feature of the distal end of the flexible liner; and a vacuum device operatively connected to the socket such that the vacuum device is operative to withdraw air from the interior of the socket; where the surface feature of the liner distal end includes at least one of an annular projection and an annular groove; and where the surface feature of the proximal end of the locking mechanism includes the other of the annular projection and the annular groove.

In a detailed embodiment, a prosthetic limb assembly may include an annular cushion forming at least a portion of the proximal end of the locking mechanism. In a detailed embodiment, the cushion may include at least one flexible rim circumferentially surrounding the cushion; and the flexible rim may sealingly engage an inner surface of the socket. In a detailed embodiment, the cushion may be constructed from a substantially resilient material.

In a detailed embodiment, the surface feature of the liner distal end may include at least one of a radially extending rib and a radially extending groove; and the surface feature of the proximal end of the locking mechanism may include at least one of a corresponding radially extending groove and a corresponding radially extending rib.

In a detailed embodiment, the plunger pin may include a gasket disposed against a flange for releasably and sealingly engaging a substantially flat annular portion of the proximal surface of the locking mechanism.

In an aspect, a locking system for a prosthetic socket may include a flexible liner shaped to accept a portion of a patient's residual limb, the flexible liner including a liner distal end including at least one surface feature; a plunger pin extending distally from the liner distal end; and a locking mechanism for mounting within a prosthetic limb socket approximate a socket distal end, the locking mechanism including a central opening sized to receive the plunger pin, the locking mechanism releasably engaging the plunger pin when the residual limb and the liner are inserted into the socket, where a proximal end of the locking mechanism includes at least one surface feature for releasably and sealingly engaging the at least one surface feature of the distal end of the flexible liner; where the surface feature of the liner distal end includes at least one of an annular projection and an annular groove; and where the surface feature of the proximal end of the locking mechanism includes the other of the annular projection and the annular groove.

In a detailed embodiment, a locking system may include a vacuum device for connection to the socket such that the vacuum device is operative to withdraw air from an interior of the socket. In a detailed embodiment, at least one surface feature of the liner distal end may include at least one annular surface feature substantially circumscribing at least one radial surface feature. In a detailed embodiment, at least one surface feature of the proximal end of the locking mechanism may include at least one annular surface feature substantially circumscribing at least one radial surface feature.

In a detailed embodiment, the proximal end of the locking mechanism may include an annular resilient cushion, the annular resilient cushion including the at least one surface feature of the proximal end of the locking mechanism. In a detailed embodiment, the cushion may include an annular rim arranged to sealingly engage an interior surface of the socket.

In a detailed embodiment, the plunger pin may include a gasket disposed against a flange for releasably and sealingly engaging a substantially flat annular portion of the proximal surface of the locking mechanism. In a detailed embodiment, the surface feature of the liner distal end may include at least one of a radially extending rib and a radially extending groove; and the surface feature of the proximal end of the locking mechanism may include at least one of a corresponding radially extending groove and a corresponding radially extending rib.

In an aspect, a method of using a prosthetic limb may include donning a flexible liner over a residual limb; inserting the residual limb and the flexible liner into a socket while causing a plunger pin extending distally from the flexible liner to enter a central opening of a locking mechanism mounted within a distal end of the socket; releasably and sealingly engaging a surface feature of a distal end of the flexible liner with a corresponding surface feature of a proximal end of the locking mechanism to provide a substantially air-tight seal substantially circumscribing the plunger pin; and withdrawing air from between the socket and the flexible liner.

In a detailed embodiment, the inserting operation may include venting air from between the socket and the flexible liner. In a detailed embodiment, causing the plunger pin to enter the central opening of the locking mechanism may include releasably retaining the plunger pin in the locking mechanism.

In a detailed embodiment, a method may include, prior to withdrawing air from between the socket and the flexible liner, placing a sealing sleeve about a proximal end of the socket to seal the socket to the flexible liner. In a detailed embodiment, a method may include supplying positive pressure to between the socket and the flexible liner to assist in removing the residual limb from the socket.

BRIEF DESCRIPTION OF THE DRAWINGS

The detailed description refers to the following figures in which.

DETAILED DESCRIPTION

The present disclosure is directed, inter alia, to systems for releasably coupling a prosthetic device to the residual limb of an amputee. More specifically, the present disclosure includes devices utilizing integrated vacuum and mechanical coupling to provide improved retention and comfort for a prosthetic device including a socket.

Figure 1:
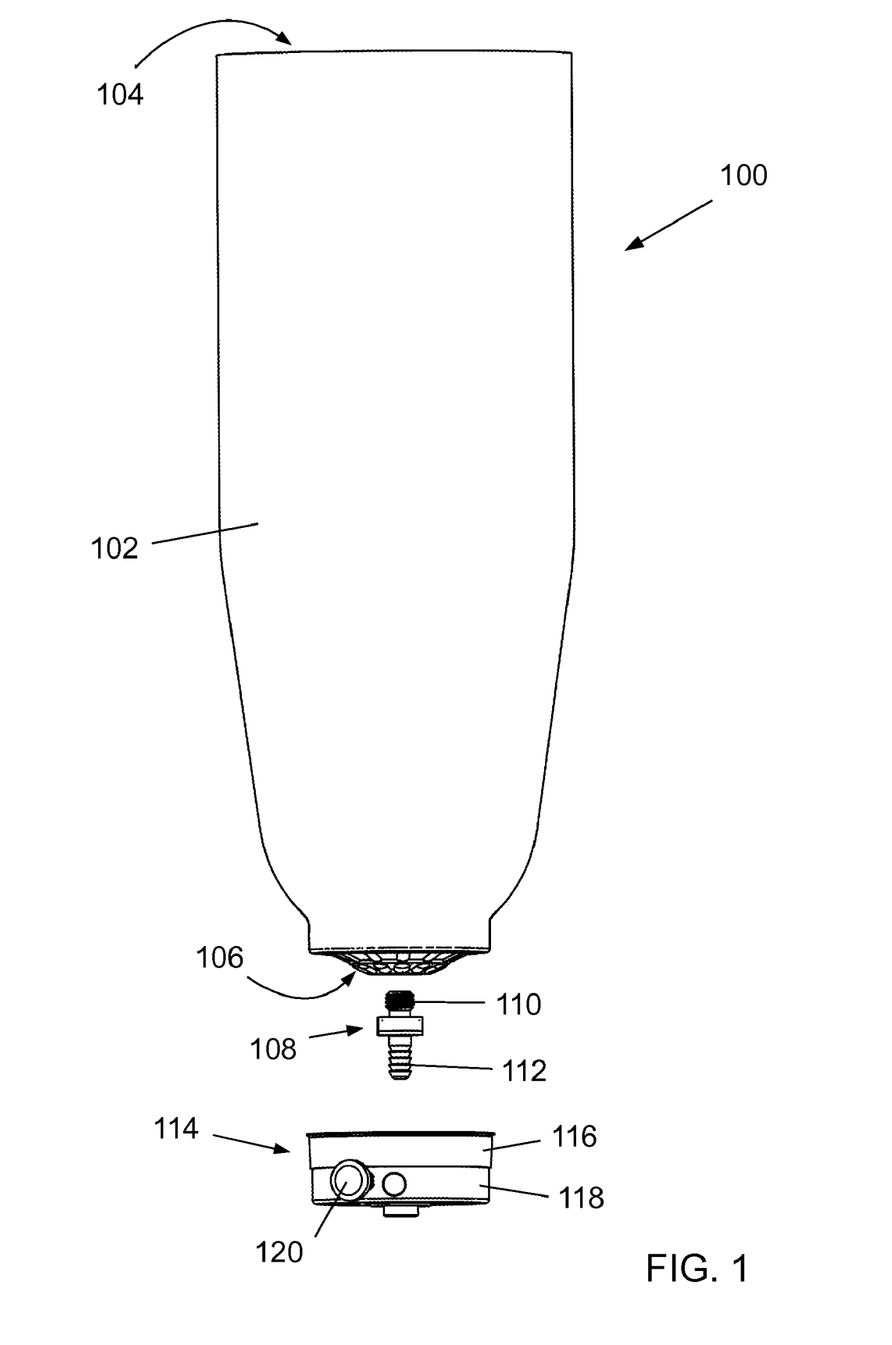
FIG. 1 is an exploded view of an exemplary locking system.

FIG. 1 is an exploded view of an exemplary locking system 100 according to the present disclosure. Substantially resilient liner 102 may be sized and/or shaped to receive an amputee's residual limb and may include a proximal end 104 and a distal end 106. Typically, the liner 102 is fabricated from a resilient material, such as silicone, such that it may be rolled-up upon and snugly fit on the residual limb. Proximal end 104 may include an opening for receiving the residual limb. A plunger pin 108 may mount to distal end 106 via threaded end 110, which may engage a threaded boss formed within the distal end 106 of liner 102. It is within the scope of the disclosure to utilize other methods of coupling plunger pin 108 to liner 102. Plunger pin 108 may also include a ratchet portion 112, which may be releasably received in a locking mechanism, such as a shuttle lock 114. Shuttle lock 114 may include a proximal cushion 116, a lower housing 118, and/or a release button 120.

Figure 2:
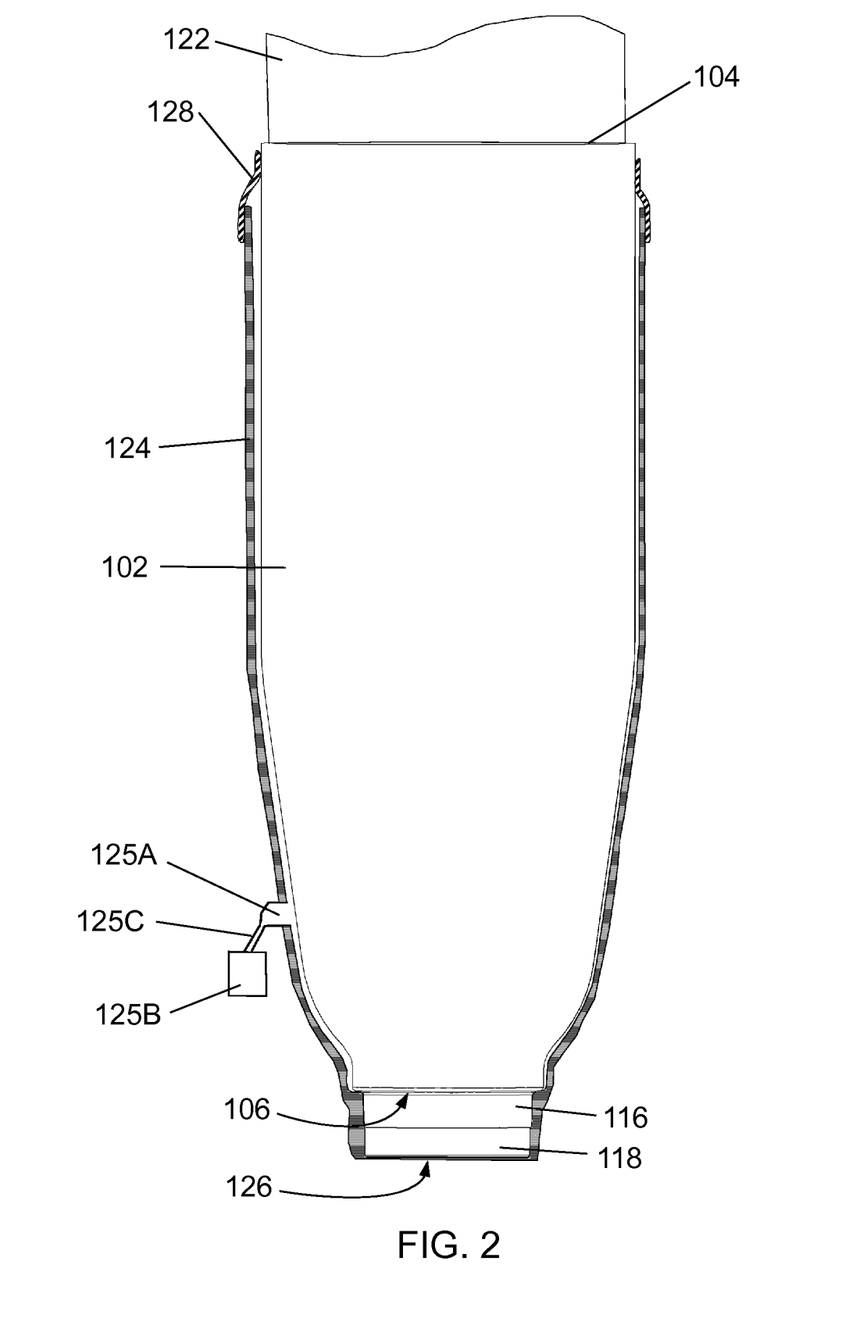
FIG. 2 is a partial cutaway view of an exemplary liner and lock assembly installed in a socket.

FIG. 2 is a partial cutaway view of an exemplary liner and lock assembly installed in a socket. Liner 102 may be worn over a residual limb 122 and may be received within substantially rigid outer socket 124 (typically fabricated from a thermoplastic material or from a resin laminate) such that distal end 106 of the liner 102 engages cushion 116 of shuttle lock 114. Socket distal end 126 may be coupled to one or more prosthetic limb components (such as a knee chassis and/or an upright assembly). A resilient sealing sleeve 128 may be worn near the proximal end of the liner 102 and covering the outer circumferential interface between the liner 102 and socket 124 such that the sealing sleeve may provide a fluidicly sealed interface near the proximal end 104 of the socket 124 between the liner 102 and the socket 124. The socket 124 may include a vacuum port 125A in a side wall thereof, which may provide a fluidic connection between the interior of the socket 124 and a vacuum device 125B.

Vacuum device 125B may comprise any device capable of withdrawing air from within the socket 124. For example, vacuum device 125B may comprise a battery-powered, electrically operated pump. Vacuum device 125B may be mounted on the prosthesis or elsewhere (such as on the patient's body) and/or may include a mechanism for monitoring and/or maintaining a desired level of vacuum within the socket 124. For example, vacuum device 125B may be mounted on an upright assembly of a prosthesis. The vacuum device 125B may be fluidicly connected to socket 124 by, for example, flexible tubing 125C and/or appropriate fittings. It is within the scope of the disclosure to utilize other vacuum devices, such as a hand-operated vacuum pump.

An exemplary vacuum device 125B may be adapted to maintain a desired vacuum level (e.g., 20-24 in Hg) within the socket 124, thereby retaining the residual limb 122 within the socket 124. For example, the vacuum device 125B may include one or more pressure sensors and a control circuit that selectively energizes an electrically driven vacuum pump to maintain the desired vacuum level within the socket 124. This vacuum retention capability may provide advantages known in the art, such as improved comfort and prevention of excessive fluid loss from the residual limb 122.

In the event of a failure of the vacuum device 125B and/or leakage of air into the socket 124 (or any other cause of loss of vacuum within the socket 124), the plunger pin 108 and shuttle lock 114 may retain the residual limb 122 within the socket 124. This mechanical backup capability may provide improved safety and reliability, as well as peace of mind for the amputee.

Figure 3:
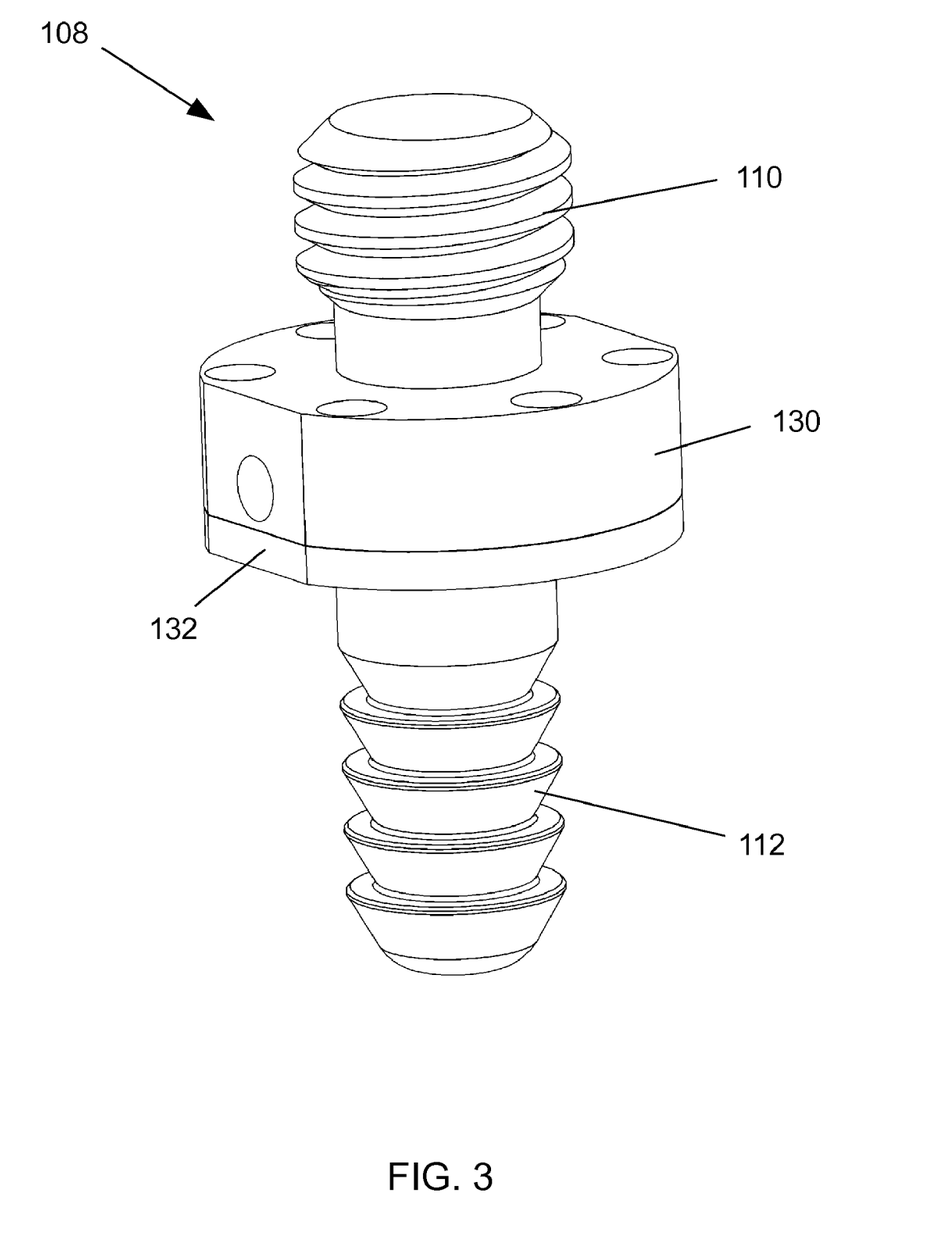
FIG. 3 is a perspective view of an exemplary plunger pin.

FIG. 3 is a perspective view of an exemplary plunger pin. An exemplary plunger pin 108 may include a flange 130 axially between threaded proximal end 110 and distal ratchet portion 112. The ratchet portion 112 may include one or more frustoconical ribs arranged axially therealong for releasably engaging the shuttle lock 114. The ribs may include tapered portions which may allow the ratchet portion 112 of the plunger pin 108 to slide relative to a spring-loaded latch (which may be part of the shuttle lock 114) in one direction while preventing movement relative to the latch in the opposite direction. In an exemplary embodiment, insertion of the ratchet portion 112 into the shuttle lock 114 may produce one or more audible "clicks," which may indicate positive engagement of the shuttle lock 114 and the plunger pin 108. A gasket 132 may be coaxially received on the plunger pin 108 against the distal end of flange 130. Gasket 132 may include a flat washer, an o-ring, or any other type of sealing member. Gasket 132 may facilitate a substantially air tight seal between the plunger pin 108 and the shuttle lock 114.

Figure 4:
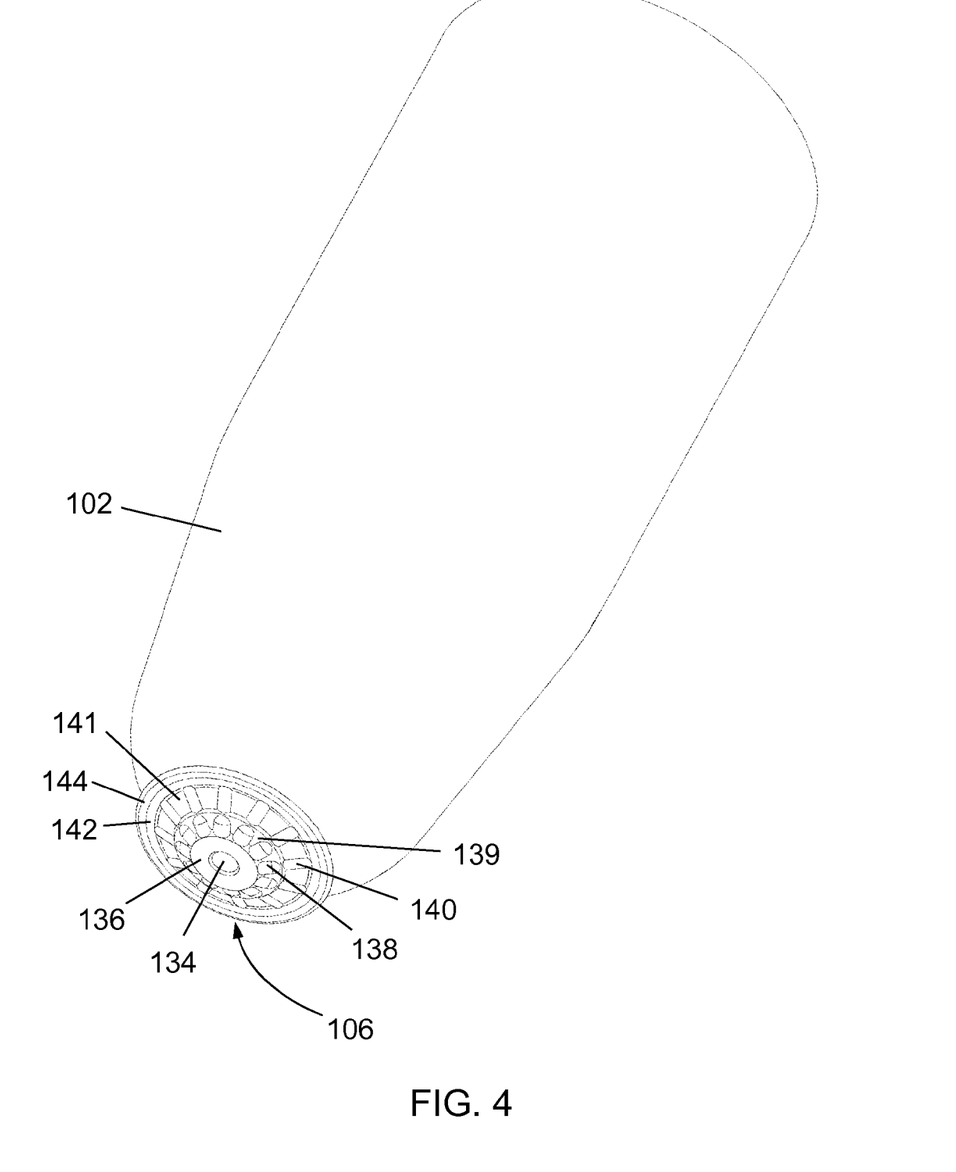
FIG. 4 is a perspective view of an exemplary liner.
Figure 5:
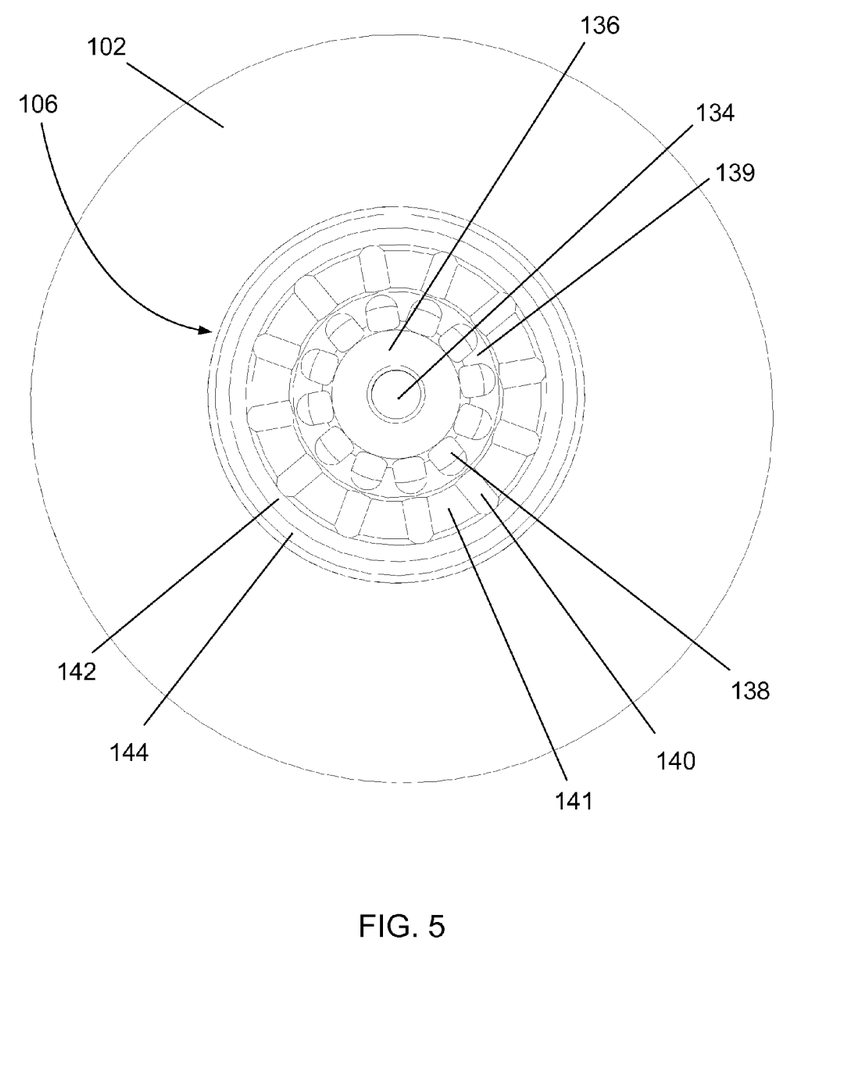
FIG. 5 is a bottom view of an exemplary liner.
Figure 6:
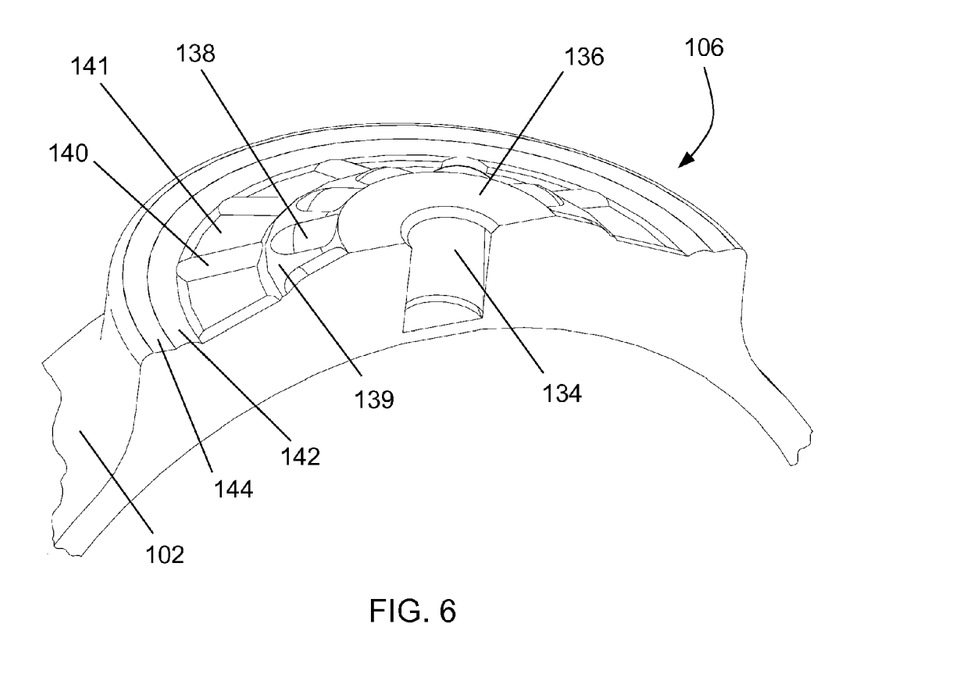
FIG. 6 is a cross-sectional view of an exemplary liner.

FIGS. 4-6 illustrate an exemplary liner 102. The distal end 106 of the liner 102 may include a threaded hole 134 for receiving the correspondingly threaded end 110 of the plunger pin 108. In some exemplary embodiments, hole 134 may be provided in an insert (such as a substantially rigid plastic and/or hard rubber insert) which may be integrated with the liner 102.

Figure 7:
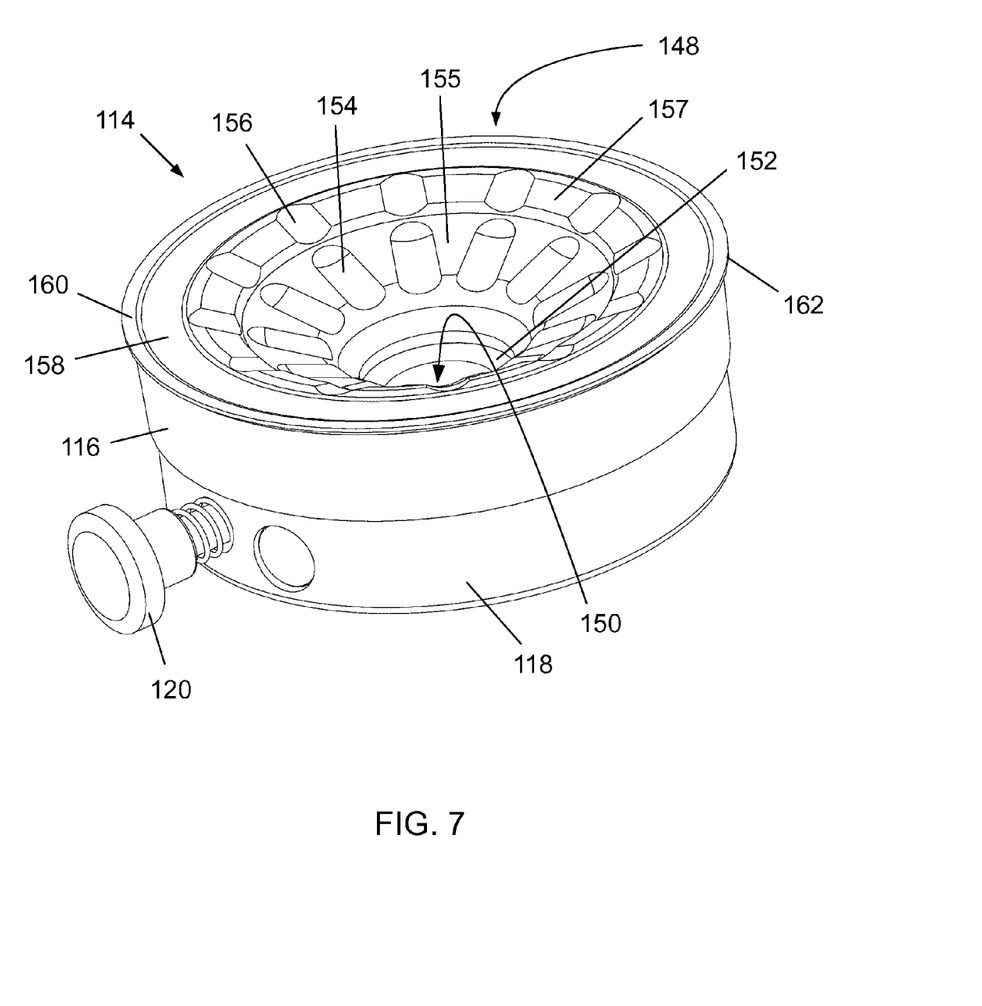
FIG. 7 is a perspective view of an exemplary shuttle lock.

In some exemplary embodiments, distal end 106 may include one or more surface features for interfacing with cushion 116 of shuttle lock 114 (see FIG. 7). For example, hole 134 may be at least partially circumscribed by a substantially flat annular surface 136. Surface 136 may be at least partially circumscribed by a first plurality of substantially radially extending ribs 138. The first plurality of radially extending ribs 138 may be uniformly distributed circumferentially about the flat surface 136, which in turn may be at least partially circumscribed by a second plurality of substantially radially extending ribs 140 uniformly distributed circumferentially thereabout. The first plurality of ribs 138 protrude distally from a first frustoconical surface 139 extending proximally from the substantially flat surface 136 at a first angle; and the second plurality of ribs 140 protrude from a second frustoconical surface 141 extending proximally from the first frustoconical surface 139, but at a smaller angle than the first frustoconical surface.

In some exemplary embodiments, the second plurality of ribs 140 may be at least partially circumscribed by one or more substantially annular rings, which may include ridges and/or depressions. For example, the second plurality of ribs 140 may be at least partially circumscribed by one or more substantially annular ridges 142, and/or depressions 144. As used herein, ridge or rib generally refers to a feature that extends above/beyond at least some adjacent portions (e.g., a convex projection), and depression or groove generally refers to a feature that is below/recessed relative to at least some adjacent portions (e.g., a concave or inset portion).

Figure 8:
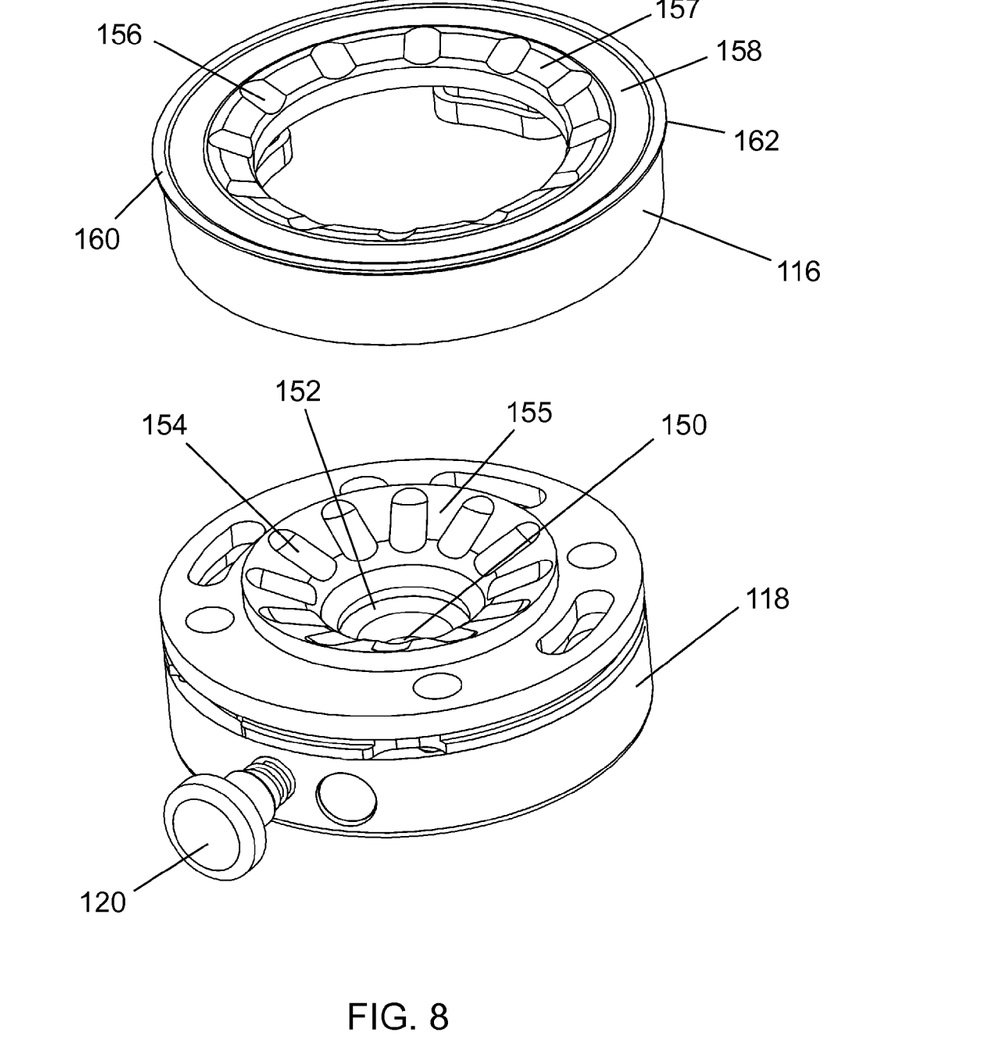
FIG. 8 is an exploded perspective view of an exemplary shuttle lock.
Figure 9:
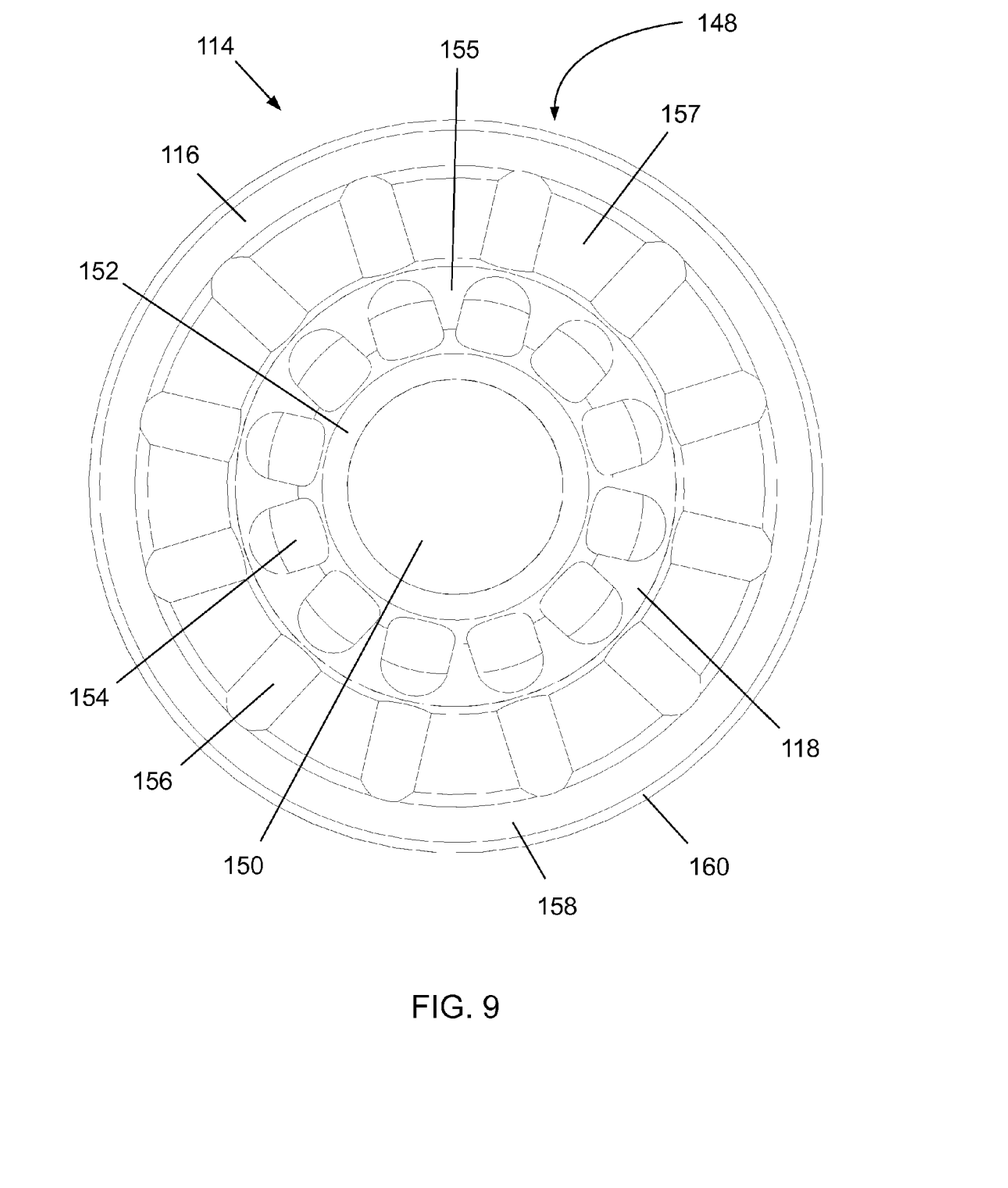
FIG. 9 is a plan view of an exemplary shuttle lock.

FIGS. 7-9 illustrate an exemplary shuttle lock 114. Exemplary lock 114 may include a cushion 116, a lower housing 118, and/or a release button 120. Proximal surface 148 of lock 114 and/or cushion 116 may include one or more surface features for interfacing with one or more corresponding surface features of distal end 106 of liner 102. For example, central hole 150 (which may receive plunger pin 108) of lock 114 may be at least partially circumscribed by a substantially flat annular surface 152, which may correspond to surface 136 of liner 102 and/or gasket 132 of plunger pin 108. Surface 152 may be at least partially circumscribed by a first plurality of substantially radially extending grooves 154, which may correspond to the first plurality of ribs 138 of liner 102. The grooves 154 recess into a frustoconical surface 155 adapted to interface with surface 139 of distal end 106. The first plurality of grooves 154 may be at least partially circumscribed by a second plurality of substantially radially extending grooves 156, which may correspond to the second plurality of ribs 140 of liner 102. The grooves 156 recess into a frustoconical surface 157 adapted to interface with surface 141 of distal end 106.

In some exemplary embodiments, the second plurality of grooves 156 may be at least partially circumscribed by one or more substantially annular rings, which may include ridges and/or depressions. For example, the second plurality of grooves 156 may be at least partially circumscribed by one or more substantially annular depressions 158 and/or ridges 160. Depression 158 (which may include a substantially flat portion) may interface with ridge 142 of liner 102. Ridge 160 may interface with depression 144 of liner 102. Such ridge/depression interfaces may provide a substantially air-tight connection between the liner 102 and the cushion 116.

In some exemplary embodiments, one or more rims 162 may circumscribe the cushion 116 and may provide a sealing fit between the cushion 116 and an inner surface of the interior of the socket 124. A sealing fit between the cushion 116 and the interior of the socket 124 may be facilitated by a tight engagement of the cushion 116 within the interior of the socket 124, with or without rims. The cushion 116 may be constructed from a resilient material, such as urethane. In some exemplary embodiments, ridge 160 may extend radially beyond the cushion 116, thereby providing a rim 162 for sealing cushion 116 to socket 124. It is within the scope of the disclosure to utilize a gasket (e.g., an o-ring) in place of or in addition to the rim 162 between the cushion 116 and the socket 124.

Referring to FIG. 8, in some exemplary embodiments, flat surface 152, grooves 154, and/or frustoconical surface 155 may be provided on a proximal surface of lower housing 118. In some exemplary embodiments, cushion 116 may include grooves 156, frustoconical surface 157, depression 158, ridge 160, and/or rim 162. As shown in FIG. 9, some exemplary embodiments may be assembled such that grooves 154 of lower housing 118 may substantially align with grooves 156 of cushion 116. Cushion 116 may be mounted substantially coaxially with lower housing 118.

Figure 10:
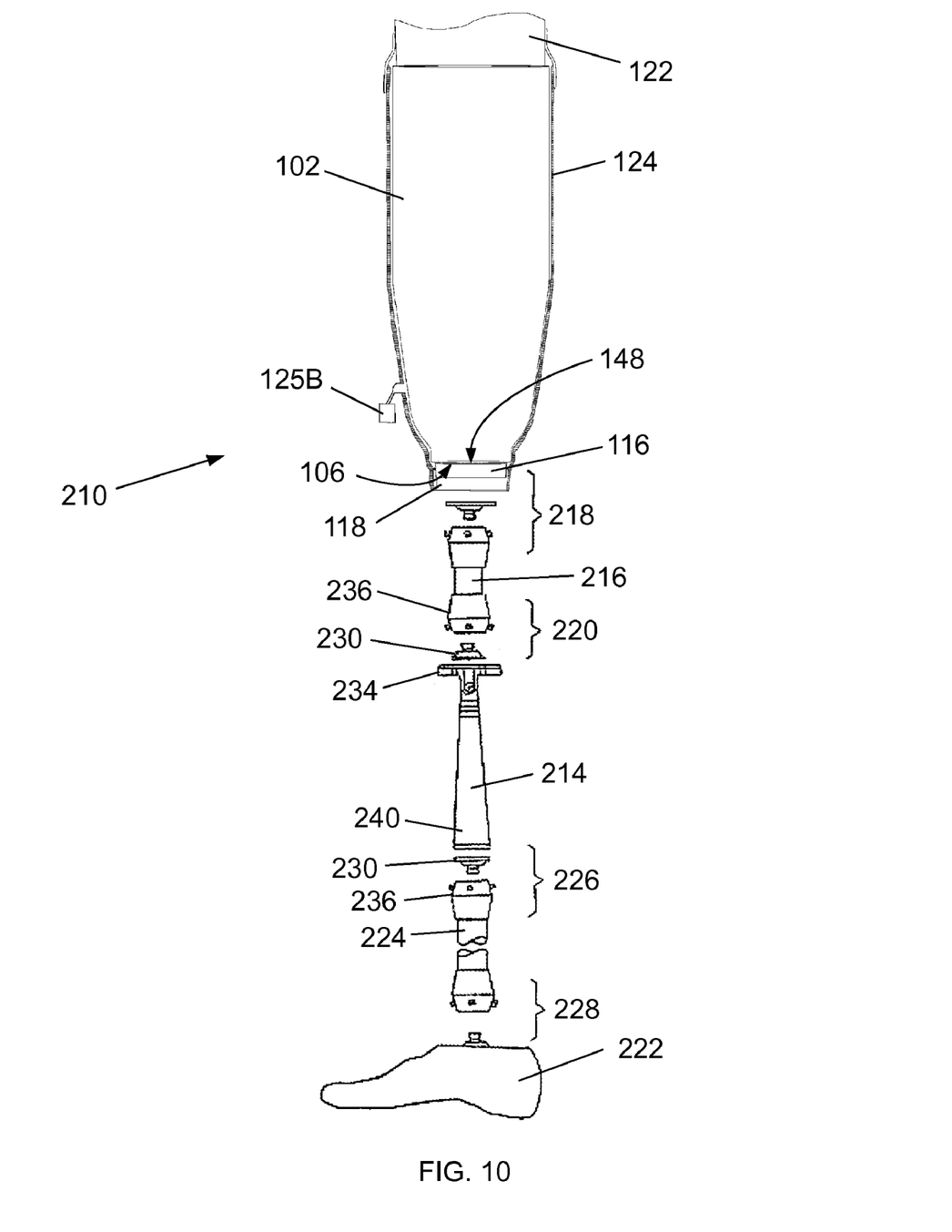
FIG. 10 is an exploded view of an exemplary prosthetic limb; all in accordance with at least some examples of the present disclosure.

FIG. 10 is an exploded view of an exemplary prosthetic limb for a transfemoral amputee including a liner 102 and shuttle lock 114 in accordance with the present disclosure. An exemplary prosthetic limb 210 may include socket 124 for receiving the patient's residual limb 122, a knee-joint assembly 214, a first pylon component 216 between the prosthetic limb socket 124 and the knee-joint assembly 214, interconnection components 218 for coupling the first pylon 216 to the prosthetic limb socket 124, interconnection components 220 for coupling the first pylon 216 to the knee-joint assembly 214, a prosthetic ankle/foot assembly 222, a second pylon 224 between the knee-joint assembly 214 and the ankle/foot assembly 222, interconnection components 226 for coupling the second pylon 224 to the knee-joint assembly 214, and interconnection components 228 for coupling the second pylon 224 to the ankle-foot assembly 222. The interconnection components 220 may include a pyramid connector 230 mounted to a proximal end of a proximal segment 234 of the knee-joint assembly 214 and a pyramid receiver 236 mounted to a distal end of the first pylon 216, for example. Interconnection components 226 may include a pyramid coupling 230 mounted to a distal end surface of a distal segment 240 of the knee-joint assembly 214 and a pyramid receiver 236 mounted to a proximal end of the second pylon 224. Various components of prosthetic limb 210 may be replaced with similar components known in the art. For example, one or both of the pyramid couplings 230 and/or receivers 236 may be replaced with adjustable pyramidal link plate assemblies.

Some exemplary liners 102 may be constructed from a flexible polymer, such as molded silicone. Exemplary liners may be worn with a wicking sock and/or may include a fabric shell. Some exemplary cushions 116 may be constructed from molded urethane, for example. Some exemplary sockets 124 may be constructed from substantially rigid polymer or may be constructed from a hard resin/fabric composite or laminate. Some exemplary shuttle locks 114 may include various plastic and metal components.

Although exemplary embodiments have been described herein as having particular arrangements of grooves, ridges, depressions, and ribs, it is within the scope of the disclosure to employ alternative arrangements of these and similar features. For example, a substantially annular groove on the distal end of a liner may seal with a substantially annular projection on a proximal portion of a shuttle lock when the liner is fully inserted into the socket, or a substantially annular projection extending from the distal end of a liner may seal with an annular groove on a proximal portion of a shuttle lock. Similarly, other corresponding sealing features between the distal end of a liner and a socket may be employed, and such sealing features may provide an air-tight seal.

Exemplary embodiments may be utilized as follows. The amputee may don the flexible liner 102 over her residual limb 122. She may insert the residual limb 122 into the substantially rigid socket 124, allowing the plunger pin 108 to enter the shuttle lock 114. Air displaced by the insertion of the residual limb 122 into the socket 124 may be vented via any gaps present between the liner 102 and the proximal end of the socket 124 and/or via vacuum port 125A. Once residual limb 122 is fully inserted into socket 124, flange 130 of plunger pin 108 may compress gasket 132 against an annular surface 152 of the shuttle lock 114 and/or the surface features of the distal end 106 of liner 102 may engage the surface features of the cushion 116, which causes an air-tight seal to be formed between the distal end 106 of the liner and the shuttle lock 114 circumscribing the plunger pin 108. The amputee may roll a sealing sleeve 128 over the proximal end of socket 124 and the liner 102 such that it seals the proximal opening of the socket 124 to the liner 102.

With the residual limb 122 and liner 102 fully inserted into the socket 124, a sealed volume may be created between the exterior surface of the liner 102 and the interior surface of the socket 124. The proximal end of socket 124 may be sealed to liner 102 using, for example, sealing sleeve 128. The inner surface at the distal end of socket 124 may be sealed to the perimeter of cushion 116 via ridge 160, for example. The proximal surface 148 of cushion 116 may be sealed to distal outer surface 106 of liner 102 and/or gasket 132. Thus, vacuum port 125A may provide the only path for fluidic communication with the sealed volume. Accordingly, a vacuum applied via vacuum port 125A may withdraw air from within the sealed volume. The amputee may operate the vacuum device 125B to withdraw air from within the sealed volume.

In some exemplary embodiments, one or more generally annular surface features of the liner 102 and the lock 114 (e.g., one or more substantially annular projections and/or substantially annular grooves) may form a sealed interface between the liner 102 and the lock 114. Such a sealed interface may provide a substantially air-tight seal. One or more generally radial surface features of the liner 102 and the lock 114 (e.g., one or more substantially radial ribs and/or substantially radial grooves) may resist rotation of the liner 102 with respect to the socket 124.

To remove the prosthesis, the amputee may turn off the vacuum device 125B. The amputee may roll the sealing sleeve 128, thereby providing an air inlet path into the socket 124 via the proximal end of socket 124, and/or the amputee may operate one or more valves allowing air into socket 124. The amputee may withdraw her residual limb 122 from the socket 124 by releasing the shuttle lock 114 (such as by depressing or withdrawing release button 120 which may disengage a latch from the ratchet portion 122 of the plunger pin 108).

In some exemplary embodiments, the amputee may operate the vacuum device 125B in a reverse direction such that it propels air into the socket 124. In such embodiments, the positive pressure supplied by the vacuum device 125B to the socket 124 may help push out the residual limb out of the socket 124.

While exemplary embodiments have been set forth above for the purpose of disclosure, modifications of the disclosed embodiments as well as other embodiments thereof may occur to those skilled in the art. Accordingly, it is to be understood that the disclosure is not limited to the above precise embodiments and that changes may be made without departing from the scope. Likewise, it is to be understood that it is not necessary to meet any or all of the stated advantages or objects disclosed herein to fall within the scope of the disclosure, since inherent and/or unforeseen advantages may exist even though they may not have been explicitly discussed herein.

What is claimed is:

1. A prosthetic limb assembly comprising:
    a flexible liner shaped to accept at least a portion of a patient's residual limb, the flexible liner including an interior, an exterior, and a liner distal end including at least one surface feature;
    a plunger pin mounted to the liner distal end;
    a socket shaped to receive the liner and the patient's residual limb, the socket including a socket interior, a proximal opening for receiving the residual limb, and a socket distal end;
    a locking mechanism mounted within the socket distal end and including a central opening sized to receive the plunger pin, the locking mechanism releasably engaging the plunger pin when the residual limb and the liner are inserted into the socket, wherein a proximal end of the locking mechanism includes at least one surface feature for releasably and sealingly engaging the at least one surface feature of the distal end of the flexible liner; and
    a vacuum device operatively connected to the socket such that the vacuum device is operative to withdraw air from the interior of the socket;
    wherein the surface feature of the liner distal end includes at least one of an annular projection and an annular groove; and
    wherein the surface feature of the proximal end of the locking mechanism includes the other of the annular projection and the annular groove.

2. The prosthetic limb assembly of claim 1, further comprising an annular cushion forming at least a portion of the proximal end of the locking mechanism.

3. The prosthetic limb assembly of claim 2,
    wherein the cushion includes at least one flexible rim circumferentially surrounding the cushion; and
    wherein the flexible rim sealingly engages an inner surface of the socket.

4. The prosthetic limb assembly of claim 3, wherein the cushion is constructed from a substantially resilient material.

5. The prosthetic limb assembly of claim 1,
    wherein the surface feature of the liner distal end includes at least one of a radially extending rib and a radially extending groove; and
    wherein the surface feature of the proximal end of the locking mechanism includes at least one of a corresponding radially extending groove and a corresponding radially extending rib.

6. The prosthetic limb assembly of claim 1, wherein the plunger pin includes a gasket disposed against a flange for releasably and sealingly engaging a substantially flat annular portion of the proximal surface of the locking mechanism.

7. A locking system for a prosthetic socket comprising:
    a flexible liner shaped to accept a portion of a patient's residual limb, the flexible liner including a liner distal end including at least one surface feature;
    a plunger pin extending distally from the liner distal end; and
    a locking mechanism for mounting within a prosthetic limb socket approximate a socket distal end, the locking mechanism including a central opening sized to receive the plunger pin, the locking mechanism releasably engaging the plunger pin when the residual limb and the liner are inserted into the socket, wherein a proximal end of the locking mechanism includes at least one surface feature for releasably and sealingly engaging the at least one surface feature of the distal end of the flexible liner;

wherein the surface feature of the liner distal end includes at least one of an annular projection and an annular groove; and wherein the surface feature of the proximal end of the locking mechanism includes the other of the annular projection and the annular groove.

8. The locking system of claim 7, further comprising a vacuum device for connection to the socket such that the vacuum device is operative to withdraw air from an interior of the socket.

9. The locking system of claim 7, wherein the at least one surface feature of the liner distal end includes at least one annular surface feature substantially circumscribing at least one radial surface feature.

10. The locking system of claim 7, wherein the at least one surface feature of the proximal end of the locking mechanism includes at least one annular surface feature substantially circumscribing at least one radial surface feature.

11. The locking system of claim 7, wherein the proximal end of the locking mechanism includes an annular resilient cushion, the annular resilient cushion including the at least one surface feature of the proximal end of the locking mechanism.

12. The locking system of claim 11, wherein the cushion includes an annular rim arranged to sealingly engage an interior surface of the socket.

13. The locking system of claim 7, wherein the plunger pin includes a gasket disposed against a flange for releasably and sealingly engaging a substantially flat annular portion of the proximal surface of the locking mechanism.

14. The prosthetic limb assembly of claim 7, wherein the surface feature of the liner distal end includes at least one of a radially extending rib and a radially extending groove; and wherein the surface feature of the proximal end of the locking mechanism includes at least one of a corresponding radially extending groove and a corresponding radially extending rib.

\* \* \* \* \*